United States Patent
Kamishita et al.

(10) Patent No.: US 11,491,219 B2
(45) Date of Patent: Nov. 8, 2022

(54) NASAL HEPATITIS B VACCINE COMPOSITION AND METHOD FOR PRODUCING SAME

(71) Applicants: TOKO YAKUHIN KOGYO CO., LTD., Osaka (JP); TOKYO METROPOLITAN INSTITUTE OF MEDICAL SCIENCE, Tokyo (JP); JAPAN as represented by DIRECTOR GENERAL of National Institute of Infectious Diseases, Tokyo (JP); KAGOSHIMA UNIVERSITY, Kagoshima (JP); NATIONAL UNIVERSITY CORPORATION EHIME UNIVERSITY, Matsuyama (JP)

(72) Inventors: Taizou Kamishita, Osaka (JP); Takashi Miyazaki, Osaka (JP); Michinori Kohara, Tokyo (JP); Takahiro Sanada, Tokyo (JP); Yoichi Hiasa, Toon (JP); Osamu Yoshida, Toon (JP); Kyoko Kohara, Kagoshima (JP); Hideki Hasegawa, Tokyo (JP)

(73) Assignees: TOKYO YAKUHIN KOGYO CO., LTD., Osaka (JP); TOKYO METROPOLITAN INSTITUTE OF MEDICAL SCIENCE, Tokyo (JP); JAPAN as represented by DIRECTOR GENERAL of National Institute of Infectious Diseases, Tokyo (JP); KAGOSHIMA UNIVERSITY, Kagoshima (JP); NATIONAL UNIVERSITY CORPORATION EHIME UNIVERSITY, Ehime (JP)

( * ) Notice: Subject to any disclaimer, the term of this patent is extended or adjusted under 35 U.S.C. 154(b) by 0 days.

(21) Appl. No.: 16/652,935

(22) PCT Filed: Oct. 4, 2018

(86) PCT No.: PCT/JP2018/037172
§ 371 (c)(1),
(2) Date: Apr. 1, 2020

(87) PCT Pub. No.: WO2019/070019
PCT Pub. Date: Apr. 11, 2019

(65) Prior Publication Data
US 2020/0261568 A1  Aug. 20, 2020

(30) Foreign Application Priority Data
Oct. 5, 2017 (JP) .............................. JP2017-195262

(51) Int. Cl.
*A61P 31/20* (2006.01)
*A61K 47/32* (2006.01)
*A61K 39/29* (2006.01)
*A61K 9/00* (2006.01)

(52) U.S. Cl.
CPC .......... *A61K 39/292* (2013.01); *A61K 9/0043* (2013.01); *A61K 9/0078* (2013.01); *A61K 47/32* (2013.01); *A61P 31/20* (2018.01)

(58) Field of Classification Search
None
See application file for complete search history.

(56) References Cited

U.S. PATENT DOCUMENTS

2007/0275012 A1  11/2007  Aguilar Rubido et al.
2009/0275668 A1* 11/2009  Kamishita ............ A61K 9/0043
                                                                514/769
2016/0015800 A1   1/2016  Hasegawa et al.

FOREIGN PATENT DOCUMENTS

| EP | 0391342 | 10/1990 |
| RU | 2 362 586 C2 | 7/2009 |
| WO | 2007/123193 | 11/2007 |
| WO | 2014/103488 | 7/2014 |

OTHER PUBLICATIONS

Aguilar et al. Development of a nasal vaccine for chronic hepatitis B infection that uses the ability of hepatitis B core antigen to stimulate a strong Th1 response against hepatitis B surface antigen. Immunology and Cell Biology (2004) 82, 539-546.*
Almeida, M. S. et al., "Nasal vaccines against hepatitis B: An update," Current Pharmaceutical Biotechnology, 2015, vol. 16, pp. 882-890.
HeberNasvac package insert, Centro para el Control Estatal de Medicamentos, Text viewed and updated Nov. 2014, 4 pages.
International Search Report of PCT/JP2018/037172, dated Nov. 20, 2018, 2 pages.
International Preliminary Report on Patentability of PCT/JP2018/037172, dated Apr. 8, 2020, 6 pages.
The extended European search report (EESR) in the corresponding European patent application No. 18864669.9, dated Jun. 8, 2021, 8 pages.
Oka, T. et al., "Influenza vaccine: enhancement of immune response by application of carboxy-vinylpolymer," Vaccine, vol. 8, No. 6, Dec. 1, 1990, pp. 573-576.
Al-Mahtab Mamun et al., "Therapeutic potential of a combined hepatitis B virus surface and core antigen vaccine in patients with chronic hepatitis B," Hepatology International, vol. 7, No. 4, Nov. 9, 2013, pp. 981-989.

(Continued)

*Primary Examiner* — Nianxiang Zou
(74) *Attorney, Agent, or Firm* — Hamre, Schumann, Mueller & Larson, P.C.

(57) ABSTRACT

The present invention relates to a hepatitis B vaccine composition for spray-administration to nasal mucosa for preventing and treating hepatitis B, which comprises hepatitis B antigen and carboxy vinyl polymer.

10 Claims, 1 Drawing Sheet

(56) References Cited

OTHER PUBLICATIONS

Office Action issue for the corresponding Russian Patent Application No. 2020115051, dated Nov. 18, 2021, 11 pages including English translation.

Pandey R. S. et al., "Evaluation of ISCOM vaccines for mucosal immunization against hepatitis B," Journal of Drug Targeting, 2010, T. 18, No. 4, pp. 282-291.

Decision of Grant issued for the corresponding Russian Patent Application No. 2020115051, dated Apr. 14, 2022, 15 pages including English translation.

Yanwei Zhong et. al., "Topic 8 Hepatitis B—Clinical, Absno: LB 17, Five years follow up study of a chronic hepatitis B patient with multidrug resistance," Hepatol Int,2014; vol. 8, S398 S399, Absno:LB8; Discussed on p. 2 of the attached Japanese Office Action.

Office Action issued for Japanese Patent Application No. 2019-547008, dated Aug. 23, 2022, 6 pages including machine translation.

\* cited by examiner s.c.　Subcutaneous administration (without CVP)
–　i.n.　Nasal administration (without CVP)
+　i.n.　Nasal administration (with CVP treated by adding outside shearing force)

NASAL HEPATITIS B VACCINE COMPOSITION AND METHOD FOR PRODUCING SAME

TECHNICAL FIELD

The present invention relates to a hepatitis B vaccine composition for spray-administration to nasal mucosa for preventing and treating hepatitis B, and a process thereof.

BACKGROUND ART

Hepatitis B is a hepatitis caused by infection with hepatitis B virus (HBV), which gets infected through blood or body fluid. The persistent infection of HBV to hepatocyte can cause chronic hepatitis, hepatic cirrhosis, hepatocellular carcinoma.

The treatment of chronic hepatitis B (CHB) is now carried out mainly by using interferon preparation (IFN) or nucleoside analog preparation (NA) as first-line therapy. In IFN therapy, some effective examples have been reported which increase immunity to sustain the growth inhibition of virus effectively, but in general, IFN therapy has low HBV clearance rate and strong side effect which has been a big problem. On the other hand, NA therapy has a high HBV clearance rate of about 95%, but the therapeutic effect is temporary and it cannot bring in complete cure. Thus, it is necessary to accept the administration over a lifetime. Accordingly, NA therapy also has big problems of compliance and medical economy, and the emergence of drug-resistant virus after long-term use has been also reported. Therefore a new therapy for CHB has been desired.

As for the prevention of HBV infection in Japan, people who have high infection risk (e.g. family members of a HBV carrier, healthcare workers) receive vaccination, which has attained some good results in major reduction of HBV carriers. For the treatment of CHB, the immunotherapy with HBV vaccine has been also tried in the past, but it has not been sufficiently successful in the treatment.

In order to try immunotherapy, the present inventors have noted the fact that there are plural antigens in HBV, and have paid attention to HBs antigen (hepatitis B surface antigen) among the plural HBV antigens, which can induce neutralizing antibody. In addition, with the recent development of technical research, it has become apparent that an acquired immunity for HBc antigen (hepatitis B nucleocapsid antigen) may contribute to the growth inhibitory of HBV and the exclusion of HBV.

In the course of time, the Center for the State Control of Medicines, Equipment and Medical Devices (CECMED) in Cuba has developed a nasal vaccine for the treatment of hepatitis B which comprises two kinds antigens, HBs antigen and HBc antigen, and then has succeeded in commercialization of product as a trade name: HeberNasvac™ (non-Patent Reference 1), after clinical testing in Bangladesh. In the administration method thereof, however, it is required to be used in conjunction with subcutaneous vaccination to gain a sufficient immune response, i.e., it is a two-cycle vaccination, not a complete vaccine for administration to nasal mucosa.

As mentioned above, a nasal vaccine formulation having broad utility which is a HBV vaccine for treatment and prevention has been desired as a next-generation hepatitis B vaccine, but it still has not completely been made.

PRIOR ART

Patent Reference

[Patent Reference 1] WO2007/123193

Non-Patent Reference

[Non-Patent Reference 1] HeberNasvac package insert

SUMMARY OF INVENTION

Technical Problem

One of the purposes of the present invention is to provide an easy-to-use hepatitis B vaccine composition for spray-administration to nasal mucosa, which does not require any parallel administration such as subcutaneous administration, and does not comprise any auxiliary ingredient having toxic concerns such as an adjuvant; a process thereof; and a method for treating and preventing hepatitis B.

Solution to Problem

The present inventors have extensively studied on the above problem and have found that a combination of (i) a gel base (material) for spray-administration to nasal mucosa comprising carboxy vinyl polymer which is treated by adding an outside shearing force to add spray-performance and (ii) 2 kinds of antigens, HBs antigen and HBc antigen, can enhance the immune induction in human beings only by nasal administration without an adjuvant. Based upon the new findings, the present invention has been accomplished. The present invention may provide the following embodiments.

[1] A hepatitis B vaccine composition for spray-administration to nasal mucosa comprising (i) hepatitis B surface antigen (HBs antigen) and/or hepatitis B nucleocapsid antigen (HBc antigen), and (ii) a gel base material comprising carboxy vinyl polymer which is treated by adding an outside shearing force to add spray-performance.

[2] The hepatitis B vaccine composition for spray-administration to nasal mucosa according to [1], wherein the amount of (i) the hepatitis B vaccine is 0.01-10 mg/mL per each antigen.

[3] The hepatitis B vaccine composition for spray-administration to nasal mucosa according to [1] or [2], which comprises 0.1 w/v % to 1.0 w/v % carboxy vinyl polymer.

[4] The hepatitis B vaccine composition for spray-administration to nasal mucosa according to any one of [1] to [3], wherein the spray-performance is to control (1) the particle-size-distribution of the sprayed composition, (2) the uniformity of spray density, and/or (3) the spray angle.

[5] The hepatitis B vaccine composition for spray-administration to nasal mucosa according to any one of claims [1] to [4], wherein the hepatitis B vaccine composition is prepared by treating a gel base material comprising 0.5 w/v % to 2.0 w/v % carboxy vinyl polymer by adding an outside shearing force to control (1) the particle-size-distribution of the sprayed composition, (2) the uniformity of spray density, and/or (3) the spray angle, as spray-performance, to give a gel base material, and then mixing the resulting gel base material with a virus stock solution comprising HBs antigen and/or HBc antigen homogeneously in a short time without stress.

[6] The hepatitis B vaccine composition for spray-administration to nasal mucosa according to any one of [1] to [5], which is prepared with a gel base material comprising carboxy vinyl polymer that is treated by adding an outside shearing force to add spray-performance which is to control that (1) as for the particle-size-distribution of the sprayed composition, the mean particle size is in a range of 50 μm to 120 μm, and the particle distribution between 10 μm and 100 μm is 50% or more, (2) the spray density is uniform to form a homogeneous full-cone shape, and (3) the spray angle is adjusted in a range of 30° to 70°.

[7] The hepatitis B vaccine composition for spray-administration to nasal mucosa according to any one of [1] to [5], which is prepared with a gel base material comprising carboxy vinyl polymer that is treated by adding an outside shearing force to add spray-performance which is to control that (1) as for the particle-size-distribution of the sprayed composition, the mean particle size is in a range of 70 μm to 100 μm, and the particle distribution between 10 μm and 100 μm is 60% or more, (2) the spray density is uniform to form a homogeneous full-cone shape, and (3) the spray angle is adjusted in a range of 40° to 60°.

[8] The hepatitis B vaccine composition for spray-administration to nasal mucosa according to any one of [1] to [7] which comprises a gel base material for spray-administration comprising carboxy vinyl polymer which is treated by adding an outside shearing force to control (1) the particle-size-distribution of the sprayed composition, (2) the uniformity of spray density, and (3) the spray angle, in order to enable a sprayable device without a pumping function to make a spray-administration.

[9] A method for preventing and/or treating hepatitis B, comprising administering the hepatitis B vaccine composition for spray-administration to nasal mucosa according to any one of [1] to [8] to a subject in need using a device which can spray a viscous formulation from naris to intra-nasal mucosa.

[10] Use of the hepatitis B vaccine composition for spray-administration to nasal mucosa according to any one of [1] to [8] for treating and/or preventing hepatitis B.

Effect of the Invention

The present invention can induce an effective immune response with a small amount of antigen in the vaccine composition comprising HBs antigen and HBc antigen as active ingredients, thereby the present invention can make it possible to provide a hepatitis B vaccine composition for spray-administration to nasal mucosa, which does not require any parallel administration such as subcutaneous administration, and does not require any adjuvant. In addition, the present invention can be administered by an easy-to-use method, has low side effect, and can bring in a sufficient immune response, thus the present invention may be used to not only prevent hepatitis B, but also treat hepatitis B, in particular, it is hopeful to completely treat CHB through continuous administration of the vaccine composition having such potent activity.

DESCRIPTION OF EMBODIMENTS

Figure 1:
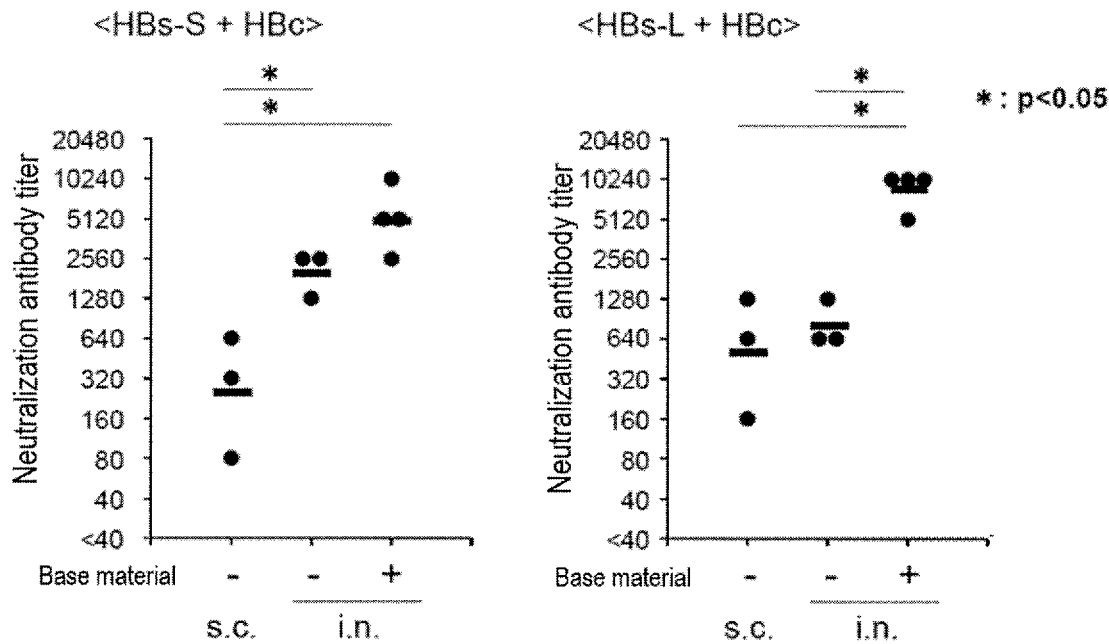
FIG. 1 shows the results of immune response, i.e., the results of the neutralizing antibody titer which was measured one week after the final inoculation. In the graphs, s.c. denotes subcutaneous-inoculation, and i.n. denotes nasal-inoculation. The base material shows CVP which is treated by adding an outside shearing force, wherein (−) denotes a base material which does not comprise the CVP, and (+) denotes a base material which comprises the CVP.

The present invention provides a hepatitis B vaccine composition for spray-administration to nasal mucosa, comprising a gel base material comprising carboxy vinyl polymer which is treated by adding an outside shearing force to add spray-performance, and a hepatitis B antigen.

The "gel base material comprising carboxy vinyl polymer which is treated by adding an outside shearing force to add spray-performance" used herein means, for example, a "gel base material comprising a skin/mucosa-adhesive agent" disclosed in WO 2007/123193, which is a base material comprising carboxy vinyl polymer and optionally comprising gellan gum, whose viscosity is adjusted by adding an outside shearing force. The actual outside shearing force disclosed in WO 2007/123193 is not a simple stirring or shaking, i.e., the operation giving the shearing force herein can be carried out with a device known by a skilled person, for example, a high-speed spinning-type emulsifying device, a colloidal mill-type emulsifying device, a high-pressure emulsifying device, a roll mill-type emulsifying device, an ultrasonic-type emulsifying device and a membrane-type emulsifying device can be used as a device giving shearing force. Especially, a homo mixer-type, a comb-type, and an intermittently-jet-stream-generating-type, high-speed spinning-type emulsifying devices are preferable. The base material is characterized in that the viscosity thereof can be adjusted to various ones by adding an outside shearing force, and the spray spreading-angle from a spray container and the spray density can be controlled to meet the purpose.

The device used in the spray-administration should not be limited as long as the device is a generally-used nasal-spray-device, and it may also include a sprayable device without a pumping function. For example, an upper-pressure-relief airless-type spray container disclosed in WO 2007/123193 (see, FIGS. 1 and 2) and WO 2007/123207 (see, FIGS. 1-11) as a multiple-dose spray container can be used for the purpose because the spray container can be set to be sprayed at any angle or any angle-range and can be used up without leftover in the container, which is suitable for the inoculation to many people in developing countries. And, as a disposable device to be used for only one person to be vaccinated, the rhinal spray nozzle disclosed in WO 2015/199130 (see, FIGS. 1-4) can be used. In the present invention, hepatitis B antigen administered with the spray-administration device can be spread at nasal mucosa widely over a long time frame, thereby the immunogenicity of the vaccine can be enhanced.

Carboxy vinyl polymer which is a material ingredient of the gel base material in the present invention is a hydrophilic polymer prepared by polymerizing acrylic acid as a main ingredient. To the gel base material, any ingredients can be added which can be chosen from pharmaceutical additives that are generally used to prepare an aqueous gel agent without any limitation.

The content of the gel base material comprising carboxy vinyl polymer which is treated by adding an outside shearing force to add spray-performance is 0.1-1.0 w/v %, preferably 0.3-0.7 w/v % as the content of carboxy vinyl polymer.

The vaccine of the present invention is characterized by comprising surface type and/or core type of hepatitis B antigen (HBs antigen, HBc antigen, respectively) as an antigen. The hepatitis B antigen used herein means hepatitis B surface antigen and hepatitis B nucleocapsid antigen which are prepared in yeast by recombinant DNA technology.

As the above-mentioned hepatitis B antigen, a virus stock solution thereof is used herein, which is purified or concentrated to be mixed with the gel base material for spray-administration to nasal mucosa. With regard to the vaccine of the present invention, the concentration of each hepatitis B virus antigen is preferably 0.01-10 mg/mL, more preferably 0.05-5 mg/mL.

Hepatitis B surface antigen (HBsAg) takes a particle form (diameter: about 50-60 nm) wherein there are a lot of antigenic proteins on the lipid membrane. The antigenic proteins are composed of originally three domains (S, Pre-S1, Pre-S2). The antigenic proteins are distinguished as follows: the antigen having all the three domains is HBsAg L-protein, the antigen lacking Pre-S1 is HBsAg M-protein, and the antigen lacking Pre-S1 and Pre-S2 is HBsAg S-protein. All the antigens can be prepared by using recombinant yeast.

An adjuvant is a generic term of substances having the modulating-activity of the immune response such as enhancement and suppression, and is used as an immuno-potentiating agent to be added to a vaccine to enhance the immunogenicity of an antigen. Until now, a lot of adjuvants have been studied. The use of an adjuvant enhances the immune effect of a vaccine, but it has disadvantages of side effects such as inflammation. Some adjuvants can be chosen as a candidate to be used in a vaccine for nasal administration, but there has not been any approved vaccine for nasal administration comprising an adjuvant because there has been no adjuvant having a pervasive safety.

The "without stress" used in the step of mixing a gel base material with a virus stock solution means that the mixing is done without heat, pressure, etc. and without a high-speed stirring.

The present inventors have found that it is possible to prepare a vaccine having a high efficacy and low side effects in spite of non-adjuvant and a lower antigen level, which is not required to be in conjunction with another administration such as subcutaneous vaccination, when the gel base material which has the above-mentioned useful spray-performance such as high adhesive property to nasal mucosa is used with the above-mentioned hepatitis B vaccine. In addition, the present inventors have also found that using a device which can spray even a gel base material having high viscosity, hepatitis B vaccine composition can be sprayed to nasal mucosa, wherein the mean particle size of the sprayed composition is in a suitable range of 50 µm to 120 µm (preferably a range of 70 µm to 100 µm), the particle-size-distribution between 10 µm and 100 µm is 50% or more (preferably, 60% or more), the spray angle from the device is set at a range of 30° to 70° (preferably, a range of 40° to 60°) so that the composition can be administered to the desired site in nasal cavity, and the spray density is uniform to form a homogeneous full-cone shape. Further the present inventors have also found its process and a method for preventing and treating hepatitis B using the composition. Based upon the new findings, the present invention has been accomplished.

The "full-cone shape" which is used to express unbiased and uniform spray density is one of sprayed shape patterns, and the full-cone shape means homogeneous whole circle. The opposite word is "hollow cone" which has a doughnut shape.

The vaccine of the present invention can comprise an additional pharmaceutically-acceptable carrier(s) besides hepatitis B virus antigens and a gel base material for spray-administration to nasal mucosa. The carrier used herein can be a carrier which is generally used in the preparation of a vaccine or a formulation for administration in nasal cavity, which includes, for example, saline, buffered saline, dextrose, water, glycerin, isotonic aqueous buffer solution, and a combination thereof. And, the vaccine of the present invention may optionally include a preservative (e.g. thimerosal), an isotonic agent, a pH regulator, a surfactant, a stabilizing agent (e.g. disodium edetate hydrate), and an inactivating agent (e.g. formalin).

The dosage of the vaccine should be decided considering the age, sex and weight of a subject, and generally it can be administered in a dose of 0.1-100 µg per one kind of antigen, preferably 0.5-10 µg, once, twice, or more times. Preferably, the vaccine is administered in plural. In this case, the interval of the administration is preferably 1 to 4 weeks.

EXAMPLE

Hereinafter, the invention is illustrated based on examples, but should not be limited thereto.

According to the methods shown below, gel base materials and hepatitis B virus stock solutions were prepared, and each gel base material and each virus stock solution were mixed as shown below to prepare hepatitis B vaccine compositions.

<Preparation of Gel Base Material>
Example of Gel Base Material (1)

| Ingredients | Amount | Process of Preparation |
|---|---|---|
| Carboxy vinyl polymer | 11.0 mg | Each ingredient shown in the left column was mixed in the ratio corresponding to each weight shown there, and stirred to become homogeneous. Then, the mixture was given an outside shearing force by a high-speed rotation with an intermittently-jet-stream-generating-type high-speed spinning-type emulsifying device. The resulting base material whose viscosity was suitably adjusted with an outside shearing force was heated at 90° C. for 20 minutes to give a gel base material. Aspect: a clear and colorless gel base material, almost odorless. pH: 7.29 Viscosity: 3,800 mPa · s |
| L-arginine | 24.0 mg | |
| Concentrated glycerin | 20.0 mg | |
| Purified water | q.s. | |
| Total | 1.0 mL | |

<Preparation of Virus Stock Solution Comprising Hepatitis B Virus Antigen>
Example of Virus Stock Solution (1)

| Ingredients | Amount |
|---|---|
| HBsAg S-protein | 0.2 mg |
| HBcAg | 0.2 mg |

| Ingredients | Amount |
|---|---|
| Sodium chloride | 8.0 mg |
| Potassium chloride | 0.2 mg |
| Disodium hydrogenphosphate (anhydrous) | 1.15 mg |
| Sodium dihydrogenphosphate (anhydrous) | 0.2 mg |
| Purified water | Total 1 mL |

Example of Virus Stock Solution (2)

| Ingredients | Amount |
|---|---|
| HBsAg L-protein | 0.2 mg |
| HBcAg | 0.2 mg |
| Sodium chloride | 8.0 mg |
| Potassium chloride | 0.2 mg |
| Disodium hydrogenphosphate (anhydrous) | 1.15 mg |
| Sodium dihydrogenphosphate (anhydrous) | 0.2 mg |
| Purified water | Total 1 mL |

<Mixture of Gel Base Material and Virus Stock Solution>

Example of virus stock solution (1) or Example of virus stock solution (2), and Example of gel base material (1) mentioned above were mixed in the ratio of 1:1 under stirring to give a homogeneous nasal hepatitis B vaccine composition (Example 1 or Example 2). The mixing under stirring can be completed softly and in a short time without giving a stress such as heat and pressure to the hepatitis B vaccine antigen. The quantities of each ingredient in the resulting hepatitis B vaccine composition, the physical properties thereof, and the spray-performances thereof derived by spraying the compositions with a suitable device are also shown below.

Example 1

| Ingredients | Amount | Physical property/ spray-performance |
|---|---|---|
| HBsAg L-protein | 0.10 mg | pH: 7.16 |
| HBcAg | 0.10 mg | Viscosity: 505 mPa · s |
| Carboxy vinyl polymer | 5.50 mg | Spray-performance in |
| L-arginine | 12.00 mg | spraying 250 µL of the |
| Concentrated glycerin | 10.00 mg | solution with a spray |
| Sodium chloride | 4.00 mg | device which has no pump |
| Potassium chloride | 0.10 mg | function: |
| Disodium hydrogenphosphate (anhydrous) | 5.75 mg | Mean particle size of sprayed formulation: 88.2 µm |
| Sodium dihydrogenphosphate (anhydrous) | 0.10 mg | Ratio of particle size between 10 µm and 100 µm: 66.3% |
| Purified water | q.s. | Spray angle from the device: 55° |
| Total | 1.0 mL | Spray density: full-cone uniformly-circle |

Example 2

| Ingredients | Amount | Physical property/ spray-performance |
|---|---|---|
| HBsAg S-protein | 0.10 mg | pH: 7.16 |
| HBcAg | 0.10 mg | Viscosity: 503 mPa · s |
| Carboxy vinyl polymer | 5.50 mg | Spray-performance in |
| L-arginine | 12.00 mg | spraying 250 µL of the |
| Concentrated glycerin | 10.00 mg | solution with a spray |
| Sodium chloride | 4.00 mg | device which has no pump |
| Potassium chloride | 0.10 mg | function: |
| Disodium hydrogenphosphate (anhydrous) | 5.75 mg | Mean particle size of sprayed formulation: 84.5 µm |
| Sodium dihydrogenphosphate (anhydrous) | 0.10 mg | Ratio of particle size between 10 µm and 100 µm: 65.9% |
| Purified water | q.s. | Spray angle from the device: 53° |
| Total | 1.0 mL | Spray density: full-cone uniformly-circle |

Nasal hepatitis B vaccine compositions which comprise no the gel base material were prepared according to the tables shown below.

Comparative Example 1

| Ingredients | Amount |
|---|---|
| HBsAg L-protein | 0.10 mg |
| HBcAg | 0.10 mg |
| Sodium chloride | 8.0 mg |
| Potassium chloride | 0.2 mg |
| Disodium hydrogenphosphate (anhydrous) | 1.15 mg |
| Sodium dihydrogenphosphate (anhydrous) | 0.2 mg |
| Purified water | q.s. |
| Total | 1.0 mL |

Comparative Example 2

| Ingredients | Amount |
|---|---|
| HBsAg S-protein | 0.10 mg |
| HBcAg | 0.10 mg |
| Sodium chloride | 8.0 mg |
| Potassium chloride | 0.2 mg |
| Disodium hydrogenphosphate (anhydrous) | 1.15 mg |
| Sodium dihydrogenphosphate (anhydrous) | 0.2 mg |
| Purified water | q.s. |
| Total | 1.0 mL |

Study of Immune Response

With regard to the nasal hepatitis B vaccine compositions which were prepared in Examples 1 and 2 and Comparative Examples 1 and 2, each antibody-inducibility was evaluated with experimental animals, treeshrews, as shown below.

(Antibody-Induction to Antibody)

Treeshrews (*Tupaia belangeri*, purchased from Kunming Institute of Zoology) to be used as experimental animals were randomly divided into 4 groups (2 groups of 4 animals and 2 groups of 3 animals). The two groups of 4 animals were antibody-induced with Examples 1 and 2 through nasal administration, and the two groups of 3 animals were antibody-induced with Comparative Examples 1 and 2 through nasal administration. The nasal spray-administration was carried out from a nostril with a high-pressure syringe and a liquid spray device. The vaccine compositions were inoculated into each treeshrew in an amount of 0.05 mL for one nostril (in total, 10 μg of each antigen for both nostrils). After the initial inoculation, the inoculation was carried out every 2 weeks totally 5 times. And then, after 4 week-interval, the inoculation was carried out one more time. The blood was collected at the time of each inoculation and one week after the final inoculation, and the neutralizing antibody titer was evaluated with each collected blood.

Separately, new 2 groups of 3 treeshrews were set, and Comparative Examples 1 and 2 were subcutaneously inoculated into each treeshrew's back in an amount of 0.1 mL (10 μg of each antigen). Then, the treeshrews were treated in the same manner as the above nasal administration test (including continuous administration, blood collection, and evaluation).

(Measurement of Neutralizing Antibody Titer and Serum IgA Antibody)

The virus fluid to be used in measuring neutralizing antibody titer was prepared by infecting human primary hepatocyte (PXB cell, made by PhoenixBio Company) with hepatitis B virus genotype C (C_JPNAT) and then cultivating it. The neutralization test was done with HepG2-NTCP30 cells, and the neutralizing antibody titer was measured in a conventional manner.

In addition, the serum IgA antibody to each antigen was measured by ELISA.

(Results)

Figure 2:
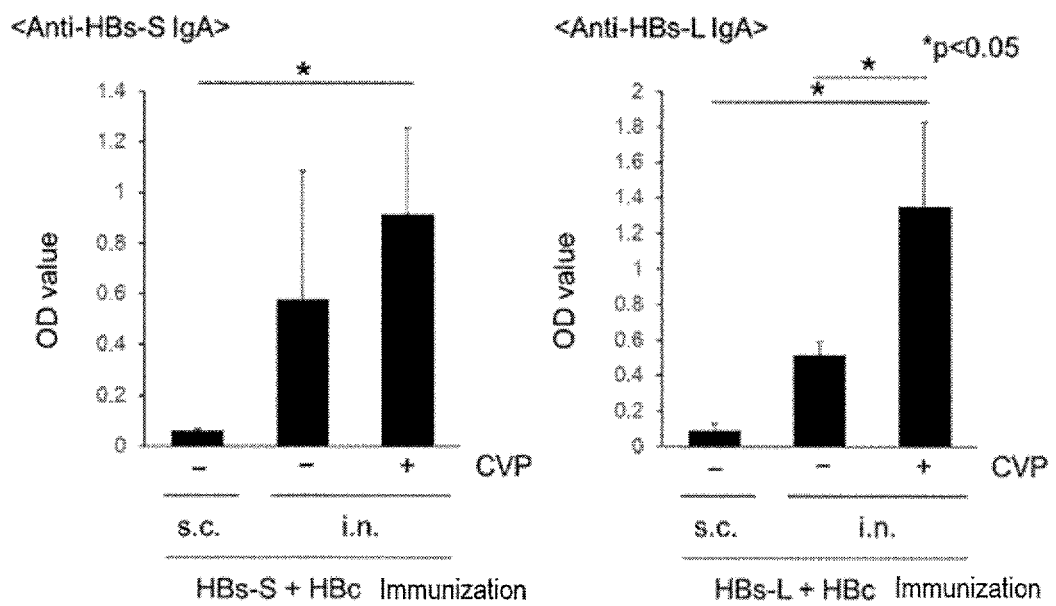
FIG. 2 shows the results of immune response, i.e., the results of the IgA antibody titer which was measured one week after the final inoculation. In the graphs, s.c. denotes subcutaneous-inoculation, and i.n. denotes nasal-inoculation. The base material shows CVP which is treated by adding an outside shearing force, wherein (−) denotes a base material which does not comprise the CVP, and (+) denotes a base material which comprises the CVP.

One week after the final inoculation, the neutralizing antibody titer and the IgA antibody titer were measured and the results are shown in Table 1 and FIGS. 1 and 2. The results show that the antibody-inducibility by nasal-inoculation was higher than that of subcutaneous-inoculation, and also show that Examples 1 and 2 comprising carboxy vinyl polymer (CVP) which was treated by adding an outside shearing force can bring in significantly-higher antibody-inducibility than Comparative Examples 1 and 2 which comprise no CVP.

TABLE 1

| administration route | base material | serum neutralizing antibody titer HBs-S + HBc | serum neutralizing antibody titer HBs-L + HBc | serum IgA antibody titer (OD value) Anti-HBs-S IgA | serum IgA antibody titer (OD value) Anti-HBs-L IgA |
| --- | --- | --- | --- | --- | --- |
| subcutaneous | without CVP | 320 | 1280 | 0.062 | 0.133 |
|  |  | 640 | 640 | 0.052 | 0.061 |
|  |  | 80 | 160 | 0.067 | 0.082 |
| nasal | without CVP | 2560 | 640 | 1.145 | 0.590 |
|  |  | 1280 | 1280 | 0.169 | 0.435 |
|  |  | 2560 | 640 | 0.417 | 0.515 |
|  | comprising CVP which is treated by adding an outside shearing force | 5120 | 10240 | 1.171 | 1.430 |
|  |  | 2560 | 5120 | 0.499 | 1.785 |
|  |  | 10240 | 10240 | 1.208 | 0.676 |
|  |  | 5120 | 10240 | 0.782 | 1.519 |

The invention claimed is:

1. A hepatitis B vaccine composition for spray-administration to nasal mucosa comprising (i) hepatitis B surface antigen (HBs antigen) and/or hepatitis B nucleocapsid antigen (HBc antigen), and (ii) a gel base material comprising a carboxy vinyl polymer that is treated by adding an outside shearing force to add a spray-performance.

2. The hepatitis B vaccine composition for spray-administration to nasal mucosa according to claim 1, wherein the amount of (i) the hepatitis B vaccine is 0.01-10 mg/mL per each antigen.

3. The hepatitis B vaccine composition for spray-administration to nasal mucosa according to claim 1, which comprises 0.1 w/v % to 1.0 w/v % of the carboxy vinyl polymer.

4. The hepatitis B vaccine composition for spray-administration to nasal mucosa according to claim 1, wherein the spray-performance is to control (1) a particle-size distribution of a sprayed composition, (2) a uniformity of a spray density, and/or (3) a spray angle.

5. The hepatitis B vaccine composition for spray-administration to nasal mucosa according to claim 1, which is prepared by treating the gel base material comprising 0.5 w/v % to 2.0 w/v % of the carboxy vinyl polymer by adding the outside shearing force to control (1) a particle-size distribution of a sprayed composition, (2) a uniformity of a spray density, and/or (3) a spray angle, as the spray-performance, to give the gel base material, and then mixing the resulting gel base material with a virus stock solution comprising the HBs antigen and/or the HBc antigen homogeneously in a short time without stress.

6. The hepatitis B vaccine composition for spray-administration to nasal mucosa according to claim 1, which is prepared with the gel base material comprising the carboxy vinyl polymer that is treated by adding the outside shearing force so as to obtain the following spray-performance:
   (1) as for a particle-size distribution of a sprayed composition, a mean particle size is in a range of 50 μm to 120 μm, and the particle-size distribution between 10 μm and 100 μm is 50% or more,
   (2) a spray density is uniform to form a homogeneous full-cone shape, and
   (3) a spray angle is adjusted in a range of 30° to 70°.

7. The hepatitis B vaccine composition for spray-administration to nasal mucosa according to claim 1, which is prepared with the gel base material comprising the carboxy vinyl polymer that is treated by adding the outside shearing force so as to obtain the following spray-performance:
   (1) as for a particle-size distribution of a sprayed composition, a mean particle size is in a range of 70 μm to 100 μm, and the particle-size distribution between 10 μm and 100 μm is 60% or more,
   (2) a spray density is uniform to form a homogeneous full-cone shape, and
   (3) a spray angle is adjusted in a range of 40° to 60°.

8. The hepatitis B vaccine composition for spray-administration to nasal mucosa according to claim 1 which comprises the gel base material comprising the carboxy vinyl polymer that is treated by adding the outside shearing force to control (1) a particle-size distribution of a sprayed composition, (2) a uniformity of a spray density, and (3) a spray angle, in order to enable a sprayable device without a pumping function to make a spray-administration.

9. A method for preventing and/or treating hepatitis B, comprising administering the hepatitis B vaccine composition for spray-administration to nasal mucosa according to claim 1 to a subject in need using a device which can spray a viscous formulation from naris to intranasal mucosa.

10. The method according to claim 9, which is for treating chronic hepatitis B (CHB), and comprises:

administering, to a subject in need thereof, an amount of the hepatitis B vaccine composition effective to bring an antibody-inducibility for the HBs antigen in the subject sufficient to completely treat CHB through continuous administration of the hepatitis B vaccine composition.

* * * * *